(12) United States Patent  
Johnson et al.

(10) Patent No.: US 9,079,809 B2  
(45) Date of Patent: *Jul. 14, 2015

(54) HIGH THROUGHPUT PROCESS FOR MANUFACTURING MOLECULAR SIEVES OF MFI FRAMEWORK TYPE

(71) Applicant: ExxonMobil Chemical Patents Inc., Baytown, TX (US)

(72) Inventors: Ivy Dawn Johnson, Lawrenceville, NJ (US); Wenyih Frank Lai, Bridgewater, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/159,166

(22) Filed: Jan. 20, 2014

(65) Prior Publication Data

US 2014/0194653 A1    Jul. 10, 2014

Related U.S. Application Data

(63) Continuation of application No. 13/789,987, filed on Mar. 8, 2013, now Pat. No. 8,673,263, which is a continuation of application No. 11/699,168, filed on Jan. 29, 2007, now Pat. No. 8,557,219, application No.

(Continued)

(51) Int. Cl.
*C01B 33/00* (2006.01)
*C01B 33/36* (2006.01)

(Continued)

(52) U.S. Cl.
CPC ............. *C07B 37/04* (2013.01); *B01J 20/3028* (2013.01); *B01J 29/04* (2013.01); *B01J 29/06* (2013.01);

(Continued)

(58) Field of Classification Search
CPC ... B01J 29/7023; B01J 29/7038; C01B 37/02; C01B 39/02; C01B 39/04; C01B 39/40
USPC .......................................... 423/700, 702, 707
See application file for complete search history.

(56) References Cited

U.S. PATENT DOCUMENTS 4,100,262 A    7/1978  Pelrine
4,439,409 A    3/1984  Puppe et al.

(Continued)

FOREIGN PATENT DOCUMENTS

CN    1 296 913    5/2001
EP    0 174 121    3/1986

(Continued)

OTHER PUBLICATIONS

U.S. Appl. No. 60/773,010, filed Feb. 14, 2006, Lai et al.

(Continued)

*Primary Examiner* — Bijay Saha
(74) *Attorney, Agent, or Firm* — Darryl M. Tyus

(57) ABSTRACT

A process for converting hydrocarbons comprising the step of contacting said hydrocarbons under conversion conditions with a crystalline molecular sieve having a pore size in the range of from about 2 to about 19 Å, said molecular sieve made by a method comprising the steps of (a) providing a mixture comprising at least one source of ions of tetravalent element (Y), at least one trivalent element hydroxide source (OH⁻), and water, said mixture having a solid-content in the range of from about 15 wt. % to about 50 wt. %. %, preferably of from about 20% to about 30%; and (b) treating said mixture to form the desired crystalline molecular sieve with stirring at crystallization conditions sufficient to obtain a weight hourly throughput from about 0.005 to about 1 hr$^{-1}$, wherein said crystallization conditions comprise a temperature in the range of from about 200° C. to about 500° C. and a crystallization time less than 100 hr, wherein said crystalline molecular sieve has a zeolite framework type of MFI.

12 Claims, 2 Drawing Sheets

X-ray diffraction pattern of Example 2

Related U.S. Application Data

14/159,166, which is a continuation of application No. 13/961,270, filed on Aug. 7, 2013, now Pat. No. 8,748,684.

(60) Provisional application No. 60/773,198, filed on Feb. 14, 2006.

(51) Int. Cl.

| | | |
|---|---|---|
| *C07B 37/04* | (2006.01) | |
| *B01J 29/04* | (2006.01) | |
| *B01J 29/06* | (2006.01) | |
| *B01J 29/40* | (2006.01) | |
| *B01J 29/70* | (2006.01) | |
| *C01B 37/02* | (2006.01) | |
| *C01B 39/02* | (2006.01) | |
| *C01B 39/04* | (2006.01) | |
| *C01B 39/40* | (2006.01) | |
| *C07C 2/66* | (2006.01) | |
| *C07C 6/12* | (2006.01) | |
| *C07C 29/36* | (2006.01) | |
| *C07C 51/235* | (2006.01) | |
| *C09B 67/26* | (2006.01) | |
| *C09B 67/54* | (2006.01) | |
| *C10G 45/64* | (2006.01) | |
| *B01J 20/30* | (2006.01) | |
| *B01J 29/80* | (2006.01) | |
| *B01J 29/86* | (2006.01) | |

(52) U.S. Cl.
CPC .............. *B01J 29/40* (2013.01); *B01J 29/7023* (2013.01); *B01J 29/7038* (2013.01); *B01J 29/80* (2013.01); *B01J 29/86* (2013.01); *C01B 37/02* (2013.01); *C01B 39/02* (2013.01); *C01B 39/04* (2013.01); *C01B 39/40* (2013.01); *C07C 2/66* (2013.01); *C07C 6/126* (2013.01); *C07C 29/36* (2013.01); *C07C 51/235* (2013.01); *C09B 67/0073* (2013.01); *C09B 67/0096* (2013.01); *C10G 45/64* (2013.01)

(56) References Cited

U.S. PATENT DOCUMENTS

| | | |
|---|---|---|
| 4,826,667 A | 5/1989 | Zones et al. |
| 4,873,067 A | 10/1989 | Valyocsik et al. |
| 4,954,325 A | 9/1990 | Rubin et al. |
| 4,973,781 A | 11/1990 | Valyocsik et al. |
| 5,236,575 A | 8/1993 | Bennett et al. |
| 5,240,892 A | 8/1993 | Klocke |
| 5,250,277 A | 10/1993 | Kresge et al. |
| 5,362,697 A | 11/1994 | Fung et al. |
| 5,558,851 A | 9/1996 | Miller |
| 5,895,769 A | 4/1999 | Lai |
| 6,077,498 A | 6/2000 | Diaz Cabanas et al. |
| 6,099,820 A | 8/2000 | Miller |
| 6,342,200 B1 | 1/2002 | Rouleau et al. |
| 6,936,744 B1 | 8/2005 | Cheng et al. |
| 2005/0013774 A1 | 1/2005 | Dakka et al. |

FOREIGN PATENT DOCUMENTS

| | | |
|---|---|---|
| EP | 0 284 206 | 9/1988 |
| EP | 0 293 032 | 11/1988 |
| EP | 0 999 182 | 5/2000 |
| EP | 1 061 046 | 12/2000 |
| EP | 1 105 348 | 6/2001 |
| EP | 1 249 428 | 10/2002 |
| JP | 61-111912 | 5/1986 |
| WO | 92/12928 | 8/1992 |
| WO | 97/17290 | 5/1997 |
| WO | 03/006160 | 1/2003 |
| WO | 03/029144 | 4/2003 |
| WO | 03/093230 | 11/2003 |
| WO | 2005/118476 | 12/2005 |
| WO | 2007/094949 | 8/2007 |

OTHER PUBLICATIONS

U.S. Appl. No. 60/773,014, filed Feb. 14, 2006, Lai et al.
U.S. Appl. No. 60/773,035, filed Feb. 14, 2006, Mertens et al.
U.S. Appl. No. 60/773,135, filed Feb. 14, 2006, Lai et al.
U.S. Appl. No. 60/773,197, filed Feb. 14, 2006, Lai et al.
U.S. Appl. No. 60/773,198, filed Feb. 14, 2006, Johnson et al.
Corma et al., "Synthesis and characterization of the MCM-22 zeolite", Zeolite 15: pp. 2-8, 1995.
Guray et al., "Synthesis of zeolite MCM-22 under rotating and static conditions", Microporous and Mesoporous Materials 31 (1999), pp. 241-251.
Inagaki et al., "Textural and Catalytic Properties of MCM-22 Zeolite Crystallized by the Vapor-Phase Transport Method", Bull. Chem. Soc. Jpn., 77, (2004), pp. 1249-1254.
Kim et al., "Synthesis of zeolites by water-organic vapor-phase transport", Microporous Materials, 1 (1993), pp. 191-200.
Lok et al., "The Role of Organic Molecules in Molecular Sieve Synthesis" Zeolites, vol. 3, Oct. 1983, pp. 282-291.
Marques et al., "Static crystallization of zeolites MCM-22 and MCM-49", Microporous and Mesoporous Materials 32 (1999), pp. 131-145.
Matsukata et al., "Synthesis of zeolites under vapor atmosphere, Effect of synthetic conditions on zeolite structure", Microporous Materials, 1 (1993) pp. 219-222.
McCusker, "Product Characterization by X-ray Powder Diffraction," Verified Syntheses of Zeolitic Materials, $2^{nd}$ Revised Edition, H. Robson, Ed., pp. 1-2.
Ravishankar et al., "Characterization and catalytic properties of zeolite MCM 22", Microporous Materials 4 (1995), pp. 83-93.
Xu et al., "A Novel Method for the Preparation of Zeolite ZSM-5", J. Chem. Soc., Chem. Commun., (1990), pp. 755-756.

FIG. 1 X-ray diffraction pattern of Example 2
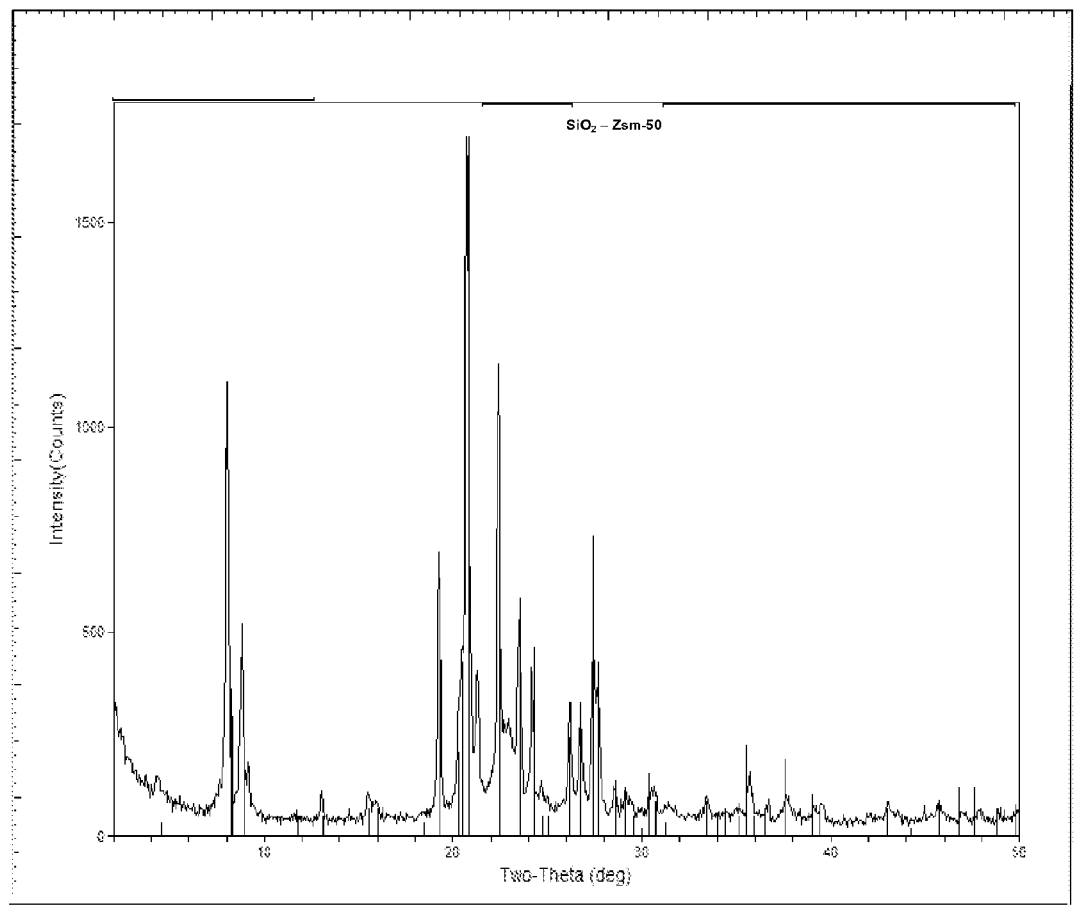

FIG. 2 SEM of Example 2 after 48 hours crystallization time
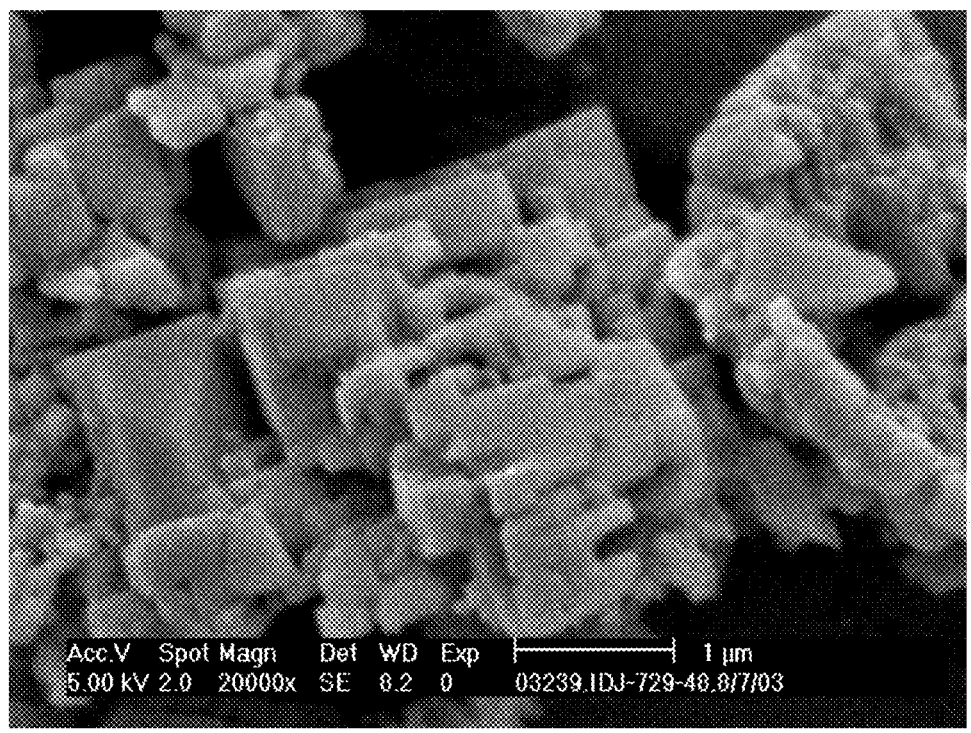

HIGH THROUGHPUT PROCESS FOR MANUFACTURING MOLECULAR SIEVES OF MFI FRAMEWORK TYPE

CROSS REFERENCE TO RELATED APPLICATION

This application is a continuation of U.S. patent application Ser. No. 13/789,987, filed Mar. 8, 2013, now U.S. Pat. No. 8,673,263, which is a continuation of U.S. application Ser. No. 11/699,168, filed Jan. 29, 2007, now U.S. Pat. No. 8,557,219 on Oct. 15, 2013, and claims the benefits of and priority to U.S. Provisional Patent Application No. 60/773,198, filed Feb. 14, 2006, and is a continuation of U.S. patent application Ser. No. 13/961,270, filed Aug. 7, 2013, now U.S. Pat. No. 8,748,684, the disclosures of which are incorporated herein by reference in their entireties.

FIELD

This invention relates to a high throughput process of manufacturing molecular sieves and the use of the same for hydrocarbon conversions.

BACKGROUND OF THIS INVENTION

Molecular sieve materials, both natural and synthetic, have been demonstrated in the past to have catalytic properties for various types of hydrocarbon conversion. Certain molecular sieves (e.g., zeolites, AlPOs, or mesoporous materials) are ordered, porous crystalline aluminosilicates having a definite crystalline structure as determined by X-ray diffraction. Since the dimensions of these pores are such as to accept for adsorption molecules of certain dimensions while rejecting those of larger dimensions, these materials have come to be known as "molecular sieves" and are utilized in a variety of industrial processes. The pores in microporous crystalline molecular sieves normally have a cross section dimension from about 2 Å to about 19 Å. This as opposed to mesoporous molecular sieves which have pore sizes between 20 Å and 1000 Å.

Molecular sieves that find application in catalysis include any of the naturally occurring or synthetic crystalline molecular sieves. Examples of these zeolites include large pore zeolites, intermediate pore size zeolites, and small pore zeolites. These zeolites and their isotypes are described in "Atlas of Zeolite Framework Types", eds. W. H. Meier, D. H. Olson and Ch. Baerlocher, Elsevier, Fifth Edition, 2001, which is hereby incorporated by reference. A large pore zeolite generally has a pore size of at least about 7 Å and includes LTL, VFI, MAZ, FAU, OFF, *BEA, and MOR framework type zeolites (IUPAC Commission of Zeolite Nomenclature). Examples of large pore zeolites include mazzite, offretite, zeolite L, VPI-5, zeolite Y, zeolite X, omega, and Beta. An intermediate pore size zeolite generally has a pore size from about 5 Å to less than about 7 Å and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, MCM-22, silicalite 1, and silicalite 2. A small pore size zeolite has a pore size from about 3 Å to less than about 5.0 Å and includes, for example, CHA, ERI, KFI, LEV, SOD, and LTA framework type zeolites (IUPAC Commission of Zeolite Nomenclature). Examples of small pore zeolites include ZK-4, ZSM-2, SAPO-34, SAPO-35, ZK-14, SAPO-42, ZK-21, ZK-22, ZK-5, ZK-20, zeolite A, chabazite, zeolite T, gmelinite, ALPO-17, and clinoptilolite.

Synthetic molecular sieves are often prepared from aqueous reaction mixtures (synthesis mixtures) comprising sources of appropriate oxides. Organic directing agents ("structure directing agent") may also be included in the synthesis mixture for the purpose of influencing the production of a molecular sieve having the desired structure. The use of such directing agents is discussed in an article by Lok et al. entitled "The Role of Organic Molecules in Molecular Sieve Synthesis" appearing in Zeolites, Vol. 3, October, 1983, pp. 282-291.

After the components of the synthesis mixture are properly mixed with one another, the synthesis mixture is subjected to appropriate crystallization conditions in an autoclave. Such conditions usually involve heating of the synthesis mixture to an elevated temperature possibly with stirring. Room temperature aging of the synthesis mixture is also desirable in some instances.

After the crystallization of the synthesis mixture is complete, the crystalline product may be recovered from the remainder of the synthesis mixture, especially the liquid contents thereof. Such recovery may involve filtering the crystals and washing these crystals with water. However, in order to remove the entire undesired residue of the synthesis mixture from the crystals, it is often necessary to subject the crystals to a high temperature calcination e.g., at 540° C., possibly in the presence of oxygen. Such a calcination treatment not only removes water from the crystals, but this treatment also serves to decompose and/or oxidize the residue of the organic directing agent which may be occluded in the pores of the crystals, possibly occupying ion exchange sites therein.

However, synthetic molecular sieves are expensive. A need exists for a high throughput process of manufacturing molecular sieves. This invention discloses a high throughput process of manufacturing molecular sieves by the combination of high solid content and high temperature. Such method of manufacturing has the advantage of low cost, short crystallization time, and high yield.

SUMMARY OF THIS INVENTION

In one embodiment, this invention relates to a process for converting hydrocarbons comprising the step of contacting said hydrocarbons under conversion conditions with a crystalline molecular sieve having a pore size in the range of from about 2 to about 19 Å, said molecular sieve made by a method comprising the steps of:

(a) providing a mixture comprising at least one source of ions of tetravalent element (Y), at least one hydroxide source (OH$^-$), and water, said mixture having a solid-content in the range of from about 15 wt. % to about 50 wt. %, preferably of from about 20% to about 30%; and (b) treating said mixture to form the desired crystalline molecular sieve with stirring at crystallization conditions sufficient to obtain a weight hourly throughput from about 0.005 to about 1 hr$^{-1}$, wherein said crystallization conditions comprise a temperature in the range of from about 200° C. to about 500° C. and a crystallization time less than 100 hr, wherein said crystalline molecular sieve has a zeolite framework type of MFI.

In another embodiment, the process further comprising the step of:
(a) separating said crystalline molecular sieve.

These and other facets of the present invention shall become apparent from the following detailed description, figure, and appended claims.

DESCRIPTION OF THE FIGURE

FIG. 1 is X-ray diffraction pattern of the crystalline material product of Example 2.

FIG. 2 is SEM image of the crystalline material product of Example 2.

DETAILED DESCRIPTION OF THIS INVENTION

Crystalline Molecular Sieve

The term "throughput" used herein means the amount of crystalline molecular sieve produced per unit time (hour) and per unit volume of the synthesis mixture (volume hourly throughput) or per unit weight of the synthesis mixture (weight hourly throughput). The higher the throughput, the more crystalline molecular sieve produced per unit volume of the reactor and per unit amount of time. Therefore, for the same amount of the crystalline molecular sieve synthesized, the higher the throughput, generally the smaller the reactor (autoclave) needed or the shorter the time required for each synthesis. The volume hourly throughput for a synthesis may be calculated by dividing the weight of the molecular sieve produced in the dried cake (the solid product after crystallization dried at 120° C. for 24 hours) with the volume of the synthesis mixture and the total time required for the crystallization (hereinafter "cycle time required for the crystallization"). The cycle time required for the crystallization is the time required for crystallization under the crystallization conditions, which does not include the time for aging the synthesis mixture, filtering, washing, and drying the product. The volume hourly throughput for a synthesis is calculated as following:

$$\text{volume hourly throughput} = \frac{\text{weight of the molecular sieve in the dried cake}}{(\text{volume of the synthesis mixture}) \times (\text{cycle time})}$$

The weight hourly throughput for a synthesis may be calculated by expressing the amount of tetravalent element in terms of its oxide and dividing the weight of the oxide of tetravalent element ($YO_2$), e.g., $SiO_2$, used in the dried cake (the solid product after crystallization dried at 120° C. for 24 hours) with the weight of the water used in the crystallization and the cycle time required for the crystallization as following:

$$\text{weight hourly throughput} = \frac{\text{weight of the } YO_2 \times \text{silica utilization}}{(\text{weight of the water}) \times (\text{crystallization time})}$$

Typical silica utilization for crystallizations is about 85%.

In one embodiment, this invention has a weight hourly throughput of at least about 0.005 $hr^{-1}$, preferably at least about 0.008 $hr^{-1}$, more preferably at least about 0.01 $hr^{-1}$, even more preferably at least about 0.02 $hr^{-1}$, and most preferably at least about 0.05 $hr^{-1}$. Optionally, this invention has a weight hourly throughput less than 1 $hr^{-1}$ or less than 0.5 $hr^{-1}$.

The weight hourly throughput of a synthesis may be adjusted by changing solid-content, amount of seed used in the synthesis gel, crystallization temperature, time for crystallization, and/or any combination thereof. The weight hourly throughput and these parameters mentioned above are interrelated. Changing one parameter may affect other parameters. For example, by increasing weight hourly throughput of a synthesis under certain crystallization conditions, e.g., crystallization temperature and time, the solid-content and/or the amount of seed crystal may have to increase.

One factor affecting the synthesis of a crystalline molecular sieve is the solid-content in a synthesis mixture. The term "solid-content" used herein means the weight ratio of the tetravalent element and the trivalent element when present in the synthesis mixture, expressed in terms of their oxides, over the water in the synthesis mixture in percentage. It can be measured by dividing the weight of the oxides in the synthesis mixture by the weight of the water in the synthesis mixture as following:

$$\text{solid-content} = \frac{\text{the weight of the oxides in the synthesis mixture}}{\text{weight of the } H_2O \text{ in the synthesis mixture}}$$

The term "high solid" used herein means that the solid-content of a synthesis mixture is at least 15 wt. %, preferably at least 18 wt. %, more preferably at least 20 wt. %, even more preferably at least 25 wt. %, and most preferably at least 30 wt. %. The solid content useful in this invention includes a range from at least about 15 wt. %, preferably at least about 18 wt. %, more preferably at least about 20 wt. %, even more preferably at least about 25 wt. %, and most preferably at least about 30 wt. % to less than 50 wt. %, preferably less than about 45 wt. %, more preferably less than about 40 wt. %, and most preferably less than about 35 wt. %.

It will be understood by a person skilled in the art that the synthesis mixture having a composition within the ranges as discussed above means that the synthesis mixture is the product of mixing, adding, reacting, or by any means of providing a mixture, wherein such product has a composition within the ranges as discussed above. The product of mixing, adding, reacting, or by any means of providing a mixture may or may not containing individual ingredients when the product was prepared. The product of mixing, adding, reacting, or by any means of providing a mixture, may even containing reaction product of individual ingredients when the product was prepared by mixing, adding, reacting, or by any means of providing a mixture.

Another factor affecting the synthesis of a crystalline molecular sieve is the temperature. High temperature, e.g., greater than 200° C., may damage the directing agent in the synthesis mixture. To perform crystallization at high temperature, more directing agent may be needed since some of the directing agent might be damaged by the caustic reactant(s) in the synthesis mixture at the high temperature. Generally, the higher the temperature, the faster the crystallization rate. However, higher temperature may damage the expensive directing agent, which may impact the product quality, e.g., final product containing impurities. The term "high temperature" as used herein means the crystallization temperature ranges from at least about 180° C., preferably at least about 190° C., more preferably at least about 200° C., even more preferably at least about 225° C., and most preferably at least about 230° C. to less than 500° C., preferably less than 400° C., more preferably less than 300° C., and most preferably less than 250° C. Another disadvantage of high temperature is narrow crystallization window.

The mixture used for synthesis of the molecular sieve may comprise a structure directing agent (template). A factor affecting the cost and the product quality of the synthesis of a crystalline molecular sieve is the amount of the directing agent. The directing agent is generally the most expensive reactant(s) in the synthesis mixture of many crystalline molecular sieves. The lower the amount of the directing agent in the synthesis mixture, the cheaper the final molecular sieve produced. The term "low directing agent" as used herein means the molar ratio of the directing agent over the tetravalent element in the synthesis mixture is less than 0.5, preferably less than 0.34, even more preferably less than 0.2, and most preferably less than 0.15.

The term "weight hourly template efficiency" used herein means the weight of crystalline molecular sieve produced per weight of directing agent used per unit time (hour). The higher the weight hourly template efficiency, the more crystalline molecular sieve produced per unit weight of the directing agent used and per unit amount of time. Therefore, for the same amount of the crystalline molecular sieve synthesized, the higher the weight hourly template efficiency, generally the cheaper the synthesis or the shorter the time required for each synthesis. The weight hourly template efficiency for a synthesis may be calculated by dividing the weight of the molecular sieve produced in the dried cake (the solid product after crystallization dried at 120° C. for 24 hours) with the weight of the directing agent used in the synthesis mixture and the total time required for the crystallization ("cycle time required for the crystallization"). The weight hourly template efficiency for a synthesis is calculated as following:

$$\text{weight hourly template efficiency} = \frac{\text{weight of the oxide of tetravalent element } (YO_2) \times \text{tetravalent element oxide utilization}}{(\text{weight of the directing agent}) \times (\text{crystallization time})}$$

Typical tetravalent element oxide, e.g., silica, utilization for crystallizations is about 85%.

In one embodiment, this invention has a weight hourly template efficiency of at least about $0.035\ hr^{-1}$, preferably at least about $0.04\ hr^{-1}$, more preferably at least about $0.05\ hr^{-1}$, even more preferably at least about $0.08\ hr^{-1}$, and most preferably at least about $0.1\ hr^{-1}$.

The weight hourly template efficiency of a synthesis may be adjusted by changing solid-content, amount of seed used in the synthesis gel, amount of template used in the synthesis gel, crystallization temperature, time for crystallization, and/or any combination thereof. The weight hourly template efficiency and these parameters mentioned above are interrelated. Changing one parameter may affect other parameters. For example, by increasing weight hourly template efficiency of a synthesis under certain crystallization conditions, e.g., crystallization temperature and time, the solid-content and/or the amount of seed crystal may have to increase or the amount of seed used in the synthesis gel may have to decrease.

Optionally the synthesis mixture may contain seed crystals. It is well known that seeding a molecular sieve synthesis mixture frequently has beneficial effects, for example in controlling the particle size of the product, avoiding the need for an organic template, accelerating synthesis, and improving the proportion of product that is of the intended framework type. In one embodiment of this invention, synthesis of the crystalline molecular sieve is facilitated by the presence of at least 0.01 wt. %, preferably 0.1 wt. %, more preferably 0.5 wt. %, even more preferably 1 wt. %, optionally from about 5 wt. % to about 20 wt. %, seed crystals based on total weight of silica of the synthesis mixture.

We discovered an improved formulation for manufacturing crystalline molecular sieves by the combination of high solid, high temperature, and optionally low directing agent, seeding at improved crystallization conditions including high temperature, stirring, and optionally recovering, recycling, and reusing the directing agent. By recovering, recycling, and reusing the directing agent, the synthesis mixture of this invention uses less costly, sometime toxic, directing agent.

In one embodiment, the crystalline molecular sieve manufactured by the process of this invention has a zeolite framework type comprising at least one of ABW, AEI, AEL, AET, AFI, AFO, CHA, EMT, FAU, FER, LEV, LTA, LTL, MAZ, MEL, MTT, NES, OFF, TON, VFI, MWW, MTW, MFI, MOR, EUO, *BEA, and MFS. In another embodiment, the crystalline molecular sieve manufactured by the process of this invention has comprises at least one of mordenite, MCM-22, MCM-49, MCM-56, ZSM-57, ZSM-5, ZSM-11, ZSM-12, ZSM-22, ZSM-23, ZSM-30, ZSM-48, ZSM-50, ZSM-48, ETS-10, ETAS-10, and ETGS-10.

The term "MCM-22 family material" (or "material of the MCM-22 family" or "molecular sieve of the MCM-22 family"), as used herein, includes one or more of:
(a) molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);
(b) molecular sieves made from a common second degree building block, being a 2-dimensional tiling of such MWW framework topology unit cells, forming a monolayer of one unit cell thickness, preferably one c-unit cell thickness;
(c) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and
(d) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize said molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575) and MCM-56 (described in U.S. Pat. No. 5,362,697). The entire contents of said patents are incorporated herein by reference.

It is to be appreciated the MCM-22 family molecular sieves described above are distinguished from conventional large pore zeolite alkylation catalysts, such as mordenite, in that the MCM-22 materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, PSH-3, SSZ-25, and ERB-1. Such molecular sieves are useful for alkylation of aromatic compounds. For example, U.S. Pat. No. 6,936,744 discloses a process for producing a monoalkylated aromatic compound, particularly cumene, comprising the step of contacting a polyalkylated aromatic compound with an alkylatable aromatic compound under at least partial liquid phase conditions and in the presence of a transalkylation catalyst to produce the monoalkylated aromatic compound, wherein the transalkylation catalyst comprises a mixture of at least two different crystalline molecular sieves, wherein each of said molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstrom.

In another embodiment, the crystalline molecular sieve of this invention has a pore size in the range of from about 2 to about 19 Å, preferably from about 2 to about 12 Å, and more preferably from about 4 to about 10 Å.

It will be understood by a person skilled in the art that the crystalline molecular sieve manufactured by the process of this invention may contain impurities, such as amorphous materials and/or other impurities (e.g., heavy metals and/or organic hydrocarbons). The crystalline molecular sieve manufactured by the process of this invention is preferably substantially free of non-crystalline material. The term "substantially free of non-crystalline material" used herein means the crystalline molecular sieve preferably contains minor proportion (less than 50 wt. %), preferably less than 20 wt. %, more preferably less than 10 wt. %, even more preferably less than 5 wt. %, and most preferably less than 1 wt. %, of such impurities non-crystalline material based on the combined weight of impurities and crystalline materials. The term "non-crystalline material" used herein means any material does not contain crystalline molecular sieve. Examples of such non-crystalline material are amorphous microporous material, amorphous mesoporous material, and amorphous macro-structure materials.

In one embodiment, the crystallization conditions comprise a temperature in the range of from about 200° C. to about 250° C., and crystallization time less than 72 hr, preferably less than 48 hours, more preferably less than 24 hours, even more preferably less than 10 hours, and most preferably less than 5 hours.

In the present synthesis method, the source of ions of tetravalent element (Y) preferably comprises solid oxide of the tetravalent element, $YO_2$, preferably about 30 wt. % solid $YO_2$ in order to obtain the crystal product of this invention. Examples of tetravalent element are silicon, germanium, and tin. When $YO_2$ is silica, the use of a silica source containing preferably about 30 wt. % solid silica, e.g., silica sold by Degussa under the trade names Aerosil or Ultrasil (a precipitated, spray dried silica containing about 90 wt. % silica), an aqueous colloidal suspension of silica, for example one sold by Grace Davison under the trade name Ludox, or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micro) favors crystal formation from the above mixture. Preferably, therefore, the $YO_2$, e.g., silica, source contains about 30 wt. % solid $YO_2$, e.g., silica, and more preferably about 40 wt. % solid $YO_2$, e.g., silica. The source of silicon may also be a silicate, e.g., an alkali metal silicate, or a tetraalkyl orthosilicate.

In another embodiment, the synthesis mixture of this invention may comprise at least one source of ions of trivalent element (X). Examples of trivalent ion are aluminum, boron, iron, and/or gallium. The source of X, e.g., aluminum, is preferably aluminum sulphate or hydrated alumina. Other aluminum sources include, for example, other water-soluble aluminum salts, sodium aluminate, or an alkoxide, e.g., aluminum isopropoxide, or aluminum metal, e.g., in the form of chips.

In one embodiment, the hydroxide source ($OH^-$) is a material containing hydroxide ion (e.g., alkali metal hydroxide, ammonium hydroxide, and alkylamine hydroxide(s)), or a material generating hydroxide ion in the synthesis mixture, such as alkali metal oxide. The alkali metal is advantageously potassium or sodium, the sodium source advantageously being sodium hydroxide or sodium aluminate.

Crystallization of the present crystalline material is carried out at stirred condition in a reactor vessel, such as for example, autoclaves. The speed of the stirring is measured by rotation per minute (RPM). In one embodiment, the stirring speed is at least 1 RPM, preferably at least 50 RPM, even more preferably, at least 100 RPM, and optionally at least 500 RPM. The stirring rate required is a function of the tip speed of the stir blades which is determined by the geometry of the reaction vessel.

The total useful range of temperatures for crystallization is from about 200° C. to about 500° C., preferably from about 210° C. to about 400° C., more preferably from about 250° C. to about 350° C., and most preferably from about 250° C. to about 300° C., for a time sufficient for crystallization to occur at the temperature used, e.g., from about 0.5 hour to about 72 hours, preferably from about 1 hour to about 48 hours, more preferably from about 5 to 24 hours, and most preferably from about 5 hours to about 12 hours. Thereafter, the crystals are separated from the liquid and recovered.

It should be realized that the synthesis mixture components can be supplied by more than one source. The synthesis mixture can be prepared either batchwise or continuously. Crystal size and crystallization time of the new crystalline material will vary with the nature of the synthesis mixture employed and the crystallization conditions.

Catalysis and Adsorption

A summary of the molecular sieves and/or zeolites, in terms of production, modification and characterization of molecular sieves, is described in the book "Molecular Sieves—Principles of Synthesis and Identification"; (R. Szostak, Blackie Academic & Professional, London, 1998, Second Edition). In addition to molecular sieves, amorphous materials, chiefly silica, aluminum silicate and aluminum oxide, have been used as adsorbents and catalyst supports. A number of long-known techniques, like spray drying, prilling, pelletizing and extrusion, have been and are being used to produce macrostructures in the form of, for example, spherical particles, extrudates, pellets and tablets of both micropores and other types of porous materials for use in catalysis, adsorption and ion exchange. A summary of these techniques is described in "Catalyst Manufacture," A. B. Stiles and T. A. Koch, Marcel Dekker, New York, 1995.

To the extent desired, however, the original metal cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for certain hydrocarbon conversion reactions. These include hydrogen, rare earth metals and metals of Groups IIA, IIIA, IVA, IB, IIB, IIIB, IVB and VIII of the Periodic Table of the Elements (IUPAC 2001).

The crystalline material of this invention, when employed either as an adsorbent or as a catalyst in an organic compound conversion process should be dehydrated, at least partially. This can be done by heating to a temperature in the range of 200° C. to 595° C. in an atmosphere such as air, nitrogen, etc. and at atmospheric, subatmospheric or superatmospheric pressures for between 30 minutes and 48 hours. Dehydration can also be performed at room temperature merely by placing the silicate in a vacuum, but a longer time is required to obtain a sufficient amount of dehydration.

When used as a catalyst, the crystalline material of this invention should be subjected to thermal treatment to remove part of all of any organic constituent. The crystalline material can also be used as a catalyst in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be in the composition by way of co-crystallization, exchanged into the composition to the extent a Group IIIA element, e.g., aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The above crystalline material, especially in its metal, hydrogen and ammonium forms can be beneficially converted to another form by thermal treatment. This thermal treatment is generally performed by heating one of these forms at a temperature of at least 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermal treated product is particularly useful in the catalysis of certain hydrocarbon conversion reactions. The thermally treated product, especially in its metal, hydrogen and ammonium forms, is particularly useful in the catalysis of certain organic, e.g., hydrocarbon, conversion reactions. Non-limiting examples of such reactions include those described in U.S. Pat. Nos. 4,954,325; 4,973,784; 4,992,611; 4,956,514; 4,962,250; 4,982,033; 4,962,257; 4,962,256; 4,992,606; 4,954,663; 4,992,615; 4,983,276; 4,982,040; 4,962,239; 4,968,402; 5,000,839; 5,001,296; 4,986,894; 5,001,295; 5,001,283; 5,012,033; 5,019,670; 5,019,665; 5,019,664; and 5,013,422, each incorporated herein by reference as to the description of said catalytic reactions.

The crystals of the crystalline material prepared by the instant invention can be shaped into a wide variety of particle sizes. Generally speaking, the particles can be in the form of a powder, a granule, or a molded product, such as an extrudate. In cases where the catalyst is molded, such as by extrusion, the crystals can be extruded before drying or partially dried and then extruded.

The crystalline material of this invention may be used as an adsorbent, such as for separating at least one component from a mixture of components in the vapor or liquid phase having differential sorption characteristics with respect to the crystalline material of this invention. Therefore, at least one component can be partially or substantially totally separated from a mixture of components having differential sorption characteristics with respect to the crystalline material of this invention by contacting the mixture with the crystalline material of this invention to selectively sorb the one component.

The crystalline material of this invention can be used to catalyze a wide variety of chemical conversion processes including many of present commercial/industrial importance. Specific examples of chemical conversion processes which are effectively catalyzed by the crystalline material of this invention, by itself or in combination with one or more other catalytically active substances including other crystalline catalysts, include the following:

(a) alkylation of aromatic hydrocarbons, e.g., benzene, with long chain olefins, e.g., $C_{14}$ olefin, with reaction conditions including a temperature of from about 340° C. to about 500° C., a pressure of from about 101 to about 20200 kPa-a, a weight hourly space velocity of from about 2 $hr^{-1}$ to about 2000 $hr^{-1}$ and an aromatic hydrocarbon/olefin molar ratio of from about 1/1 to about 20/1, to provide long chain alkyl aromatics which can be subsequently sulfonated to provide synthetic detergents;

(b) alkylation of aromatic hydrocarbons with gaseous olefins to provide short chain alkyl aromatic compounds, e.g., the alkylation of benzene with propylene to provide cumene, with reaction conditions including a temperature of from about 10° C. to about 125° C., a pressure of from about 101 to about 3030 kPa-a, and an aromatic hydrocarbon weight hourly space velocity (WHSV) of from 5 $hr^{-1}$ to about 50 $hr^{-1}$;

(c) alkylation of reformate containing substantial quantities of benzene and toluene with fuel gas containing $C_5$ olefins to provide, inter alia, mono and dialkylates with reaction conditions including a temperature of from about 315° C. to about 455° C., a pressure of from about 3000 to about 6000 kPa-a, a WHSV-olefin of from about 0.4 $hr^{-1}$ to about 0.8 $hr^{-1}$, a WHSV-reformate of from about 1 $hr^{-1}$ to about 2 $hr^{-1}$ and a gas recycle of from about 1.5 to 2.5 vol/vol fuel gas feed;

(d) alkylation of aromatic hydrocarbons, e.g., benzene, toluene, xylene and naphthalene, with long chain olefins, e.g., $C_{14}$ olefin, to provide alkylated aromatic lube base stocks with reaction conditions including a temperature of from about 160° C. to about 260° C. and a pressure of from about 2600 to 3500 kPa-a;

(e) alkylation of phenols with olefins or equivalent alcohols to provide long chain alkyl phenols with reaction conditions including a temperature of from about 200° C. to about 250° C., a pressure of from about 1500 to 2300 kPa-a and a total WHSV of from about 2 hr$^{-1}$ to about 10 hr$^{-1}$;

(f) conversion of light paraffins to olefins and aromatics with reaction conditions including a temperature of from about 425° C. to about 760° C. and a pressure of from about 170 to about 15000 kPa-a;

(g) conversion of light olefins to gasoline, distillate and lube range hydrocarbons with reaction conditions including a temperature of from about 175° C. to about 375° C. and a pressure of from about 800 to about 15000 kPa-a;

(h) two-stage hydrocracking for upgrading hydrocarbon streams having initial boiling points above about 260° C. to premium distillate and gasoline boiling range products in a first stage using the crystalline material of this invention in combination with a Group VIII metal as catalyst with effluent therefrom being reaction in a second stage using zeolite Beta, also in combination with a Group VIII metal, as catalyst, the reaction conditions including a temperature of from about 340° C. to about 455° C., a pressure of from about 3000 to about 18000 kPa-a, a hydrogen circulation of from about 176 to about 1760 liter/liter and a liquid hourly space velocity (LHSV) of from about 0.1 to 10 hr$^{-1}$;

(i) a combination hydrocracking/dewaxing process in the presence of the crystalline material of this invention and a hydrogenation component as catalyst, or a mixture of such catalyst and zeolite Beta, with reaction conditions including a temperature of from about 350° C. to about 400° C., a pressure of from about 10000 to about 11000 kPa-a, an LHSV of from about 0.4 to about 0.6 and a hydrogen circulation of from about 528 to about 880 liter/liter;

(j) reaction of alcohols with olefins to provide mixed ethers, e.g., the reaction of methanol with isobutene and/or isopentene to provide methyl-t-butyl ether (MTBE) and/or t-amyl methyl ether (TAM) with conversion conditions including a temperature of from about 20° C. to about 200° C., a pressure of from 200 to about 20000 kPa-a, a WHSV (gram-olefin per hour gram-zeolite) of from about 0.1 hr$^{-1}$ to about 200 hr$^{-1}$ and an alcohol to olefin molar feed ratio of from about 0.1/1 to about 5/1;

(k) toluene disproportionations with C$_9$+ aromatics as co-feed with reaction conditions including a temperature of from about 315° C. to about 595° C., a pressure of from about 101 to about 7200 kPa-a, a hydrogen/hydrocarbon molar ratio of from about 0 (no added hydrogen) to about 10 and a WHSV of from about 0.1 hr$^{-1}$ to about 30 hr$^{-1}$;

(l) preparation of the pharmaceutically-active compound 2-(4-isobutylphenyl)propionic acid, i.e., ibuprofen, by reacting isobutylbenzene with propylene oxide to provide the intermediate 2-(4-isobutylphenyl)propanol followed by oxidation of the alcohol to the corresponding carboxylic acid;

(m) use as an acid-binding agent in the reaction of amines with heterocyclic fiber-reactive components in preparation of dyes to prepare practically salt-free reactive dye-containing solution, as in German Patent No. DE 3,625,693, incorporated entirely herein by reference;

(n) as the absorbent for separating 2,6-toluene diisocyanate (2,6-TDI) from isomers if TDI as in U.S. Pat. No. 4,721,807, incorporated entirely herein by reference, whereby a feed mixture comprising 2,6-TDI and 2,4-TDI is contacted with the present crystalline material which has been cation-exchanged with K ions to absorb the 2,6-TDI, followed by recovering the 2,6-TDI by desorption with desorbent material comprising toluene;

(o) as the absorbent for separating 2,4-TDI from its isomers as in U.S. Pat. No. 4,721,806, incorporated entirely herein by reference, whereby a feed mixture comprising 2,4-TDI and 2,6-TDI is contact with the present crystalline material which has been cation-exchanged with Na, Ca Li and/or Mg ions to absorb the 2,4-TDI, followed by recovering the 2,4-TDI by desorption with desorbent material comprising toluene; and (p) in a process for decreasing the durene content of a 90-200° C.+ bottoms fraction obtained from the catalytic conversion of methanol to gasoline which comprises contacting said durene-containing bottoms fraction with hydrogen over a catalyst of the present crystalline material with a hydrogenation metal, at conditions including a temperature of from about 230° C. to about 425° C. and a pressure of from about 457 to about 22000 kPa-a.

In an embodiment, the molecular sieves of this invention may be used in processes that co-produce phenol and ketones that proceed through benzene alkylation, followed by formation of the alkylbenzene hydroperoxide and cleavage of the alkylbenzene hydroperoxide into phenol and ketone. In such processes, the molecular sieves of this invention are used in the first step, that is, benzene alkylation. Examples of such processes includes processes in which benzene and propylene are converted to phenol and acetone, benzene and C4 olefins are converted to phenol and methyl ethyl ketone, such as those described for example in international application PCT/EP2005/008557, benzene, propylene and C4 olefins are converted to phenol, acetone and methyl ethyl ketone, which, in this case can be followed by conversion of phenol and acetone to bis-phenol-A as described in international application PCT/EP2005/008554, benzene is converted to phenol and cyclohexanone, or benzene and ethylene are converted to phenol and methyl ethyl ketone, as described for example in PCT/EP2005/008551.

The molecular sieves of this invention are useful in benzene alkylation reactions where selectivity to the monoalkylbenzene is required. Furthermore, the molecular sieves of this invention is particularly useful to produce selectively sec-butylbenzene from benzene and C4 olefin feeds that are rich in linear butenes, as described in international application PCT/EP2005/008557. Preferably, this conversion is carried out by co-feeding benzene and the C4 olefin feed with the catalyst of the present invention, at a temperature of about 60° C. to about 260° C., for example of about 100° C. to 200° C., a pressure of 7000 kPa-a or less, and a feed weight hourly space velocity (WHSV) based on C$_4$ alkylating agent of from about 0.1 to 50 hr$^{-1}$ and a molar ratio of benzene to C$_4$ alkylating agent from about 1 to about 50.

The molecular sieves of this invention are also useful catalyst for transalkylations, such as, for example, polyalkylbenzene transalkylations.

In the case of many catalysts, it is desired to incorporate the new crystal with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the new crystal, i.e., combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dictite, narcite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the new crystal can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided crystalline material and inorganic oxide matrix vary widely, with the crystal content in the range of from about 1 to about 90 percent by weight and more usually, particularly when the composite is prepared in the form of beads, in the range of about 2 to about 80 wt. % of the composite.

The following examples illustrate exemplary preferred embodiments:

EXAMPLES

The SEM images were obtained on a JEOL JSM-6340F Field Emission Scanning Electron Microscope (SEM), using a magnification at a voltage of 2 keV.

In these examples, the XRD diffraction patterns of the as-synthesized materials were recorded on an X-Ray Powder Diffractometer using copper Kα radiation in the 2θ range of 2 to 40 degrees.

Comparative Example A

A synthesis mixture was prepared containing the following ingredients: a sodium aluminate solution (12.34 wt. % NaOH and 3.06 wt. % Al(OH)$_3$ in water, Alcoa Corporation, Pittsburgh, Pa., USA), a 50 wt. % solution of tetraethyl ammonium bromide (R) in water (Sachem Chemicals), Ultrasil VN 35P (92.4 wt. % of SiO$_2$, Degussa) and a 50 wt. % NaOH solution in water. The synthesis mixture had the following molar composition:

$$0.16Na_2O:0.033Al_2O_3:0.011R:SiO_2:58H_2O$$

The mixture was transferred to an autoclave and heated to 171° C. with a ramp rate of 25° C./hr, while stirring at 250 rotations per minute ("RPM"). The crystallization was continued for 165 hrs at 171° C.

After crystallization a solid product was recovered from the crystallization mixture, washed, and dried at 120° C. XRD analysis of the dried solid product showed it to be a mixture of mordenite and ZSM-5. The yields, solids content, and hourly throughput are summarized in Table 1 below.

Comparative Example B

A synthesis mixture was prepared containing the following ingredients: a sodium aluminate solution (12.34 wt. % NaOH and 3.06 wt. % Al(OH)$_3$ in water, Alcoa Corporation, Pittsburgh, Pa., USA), a 50 wt. % solution of tetraethyl ammonium bromide (R) in water (Sachem Chemicals), Ultrasil VN 35P (92.4 wt. % of SiO$_2$, Degussa) and a 50 wt. % NaOH solution in water. The synthesis mixture had the following molar composition:

$$0.17Na_2O:0.036Al_2O_3:0.011R:SiO_2:25H_2O$$

The mixture was transferred to an autoclave and heated to 138° C. with a ramp rate of 25° C./hr, while stirring at 250 rotations per minute ("RPM"). The crystallization was continued for 72 hrs at 138° C.

After crystallization a solid product was recovered from the crystallization mixture, washed, and dried at 120° C. XRD analysis of the dried solid product showed it to be a mixture of mordenite and ZSM-5. The yields, solids content, and hourly throughput are summarized in Table 1 below.

Example 1

A synthesis mixture was prepared containing the following ingredients: a sodium aluminate solution (12.34 wt. % NaOH and 3.06 wt. % Al(OH)$_3$ in water, Alcoa Corporation, Pittsburgh, Pa., USA), a 60 wt. % solution of triethylene tetraamine (R) in water (Sachem Chemicals), Ultrasil VN 35P (92.4 wt. % of SiO$_2$) and a 50 wt. % NaOH solution in water. The synthesis mixture had the following molar composition:

$$0.06Na_2O:0.05Al_2O_3:1.241R:SiO_2:20H_2O$$

The mixture was transferred to an autoclave and heated to 250° C. with a ramp rate of 25° C./hr. The crystallization was continued for 8 hrs at 250° C.

After crystallization a solid product was recovered from the crystallization mixture, washed, and dried at 120° C. XRD of the dried solid product showed it to be a mixture of mordenite and ZSM-5. The yields, solids content, and hourly throughput are summarized in Table 1 below.

Comparative Example C

A synthesis mixture was prepared containing the following ingredients: a sodium tetraborate decahydrate (NaB$_4$O$_7$.10H$_2$O), a 50 wt. % solution of tetraethyl ammonium bromide (R) in water (Sachem Chemicals), Ultrasil VN 35P (92.4 wt. % of SiO$_2$) and a 50 wt. % NaOH solution in water. The synthesis mixture had the following molar composition:

$$0.0315Na_2O:0.0013B_2O_3:0.01R:SiO_2:21H_2O$$

The mixture was transferred to an autoclave and heated to 160° C. with a ramp rate of 25° C./hr. The crystallization was continued for 72 hrs at 160° C.

After crystallization a solid product was recovered from the crystallization mixture, washed, and dried at 120° C. XRD of the dried solid product showed it to be ZSM-50. The yields, solids content, and hourly throughput are summarized in Table 1 below.

Example 2

A synthesis mixture was prepared containing the following ingredients: a sodium tetraborate decahydrate (NaB$_4$O$_7$.10H$_2$O), a 50 wt. % solution of tetraethyl ammonium bromide (R) in water (Sachem Chemicals), Ultrasil VN 35P (92.4 wt. % of SiO$_2$) and a 50 wt. % NaOH solution in water. The synthesis mixture had the following molar composition:

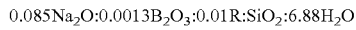
0.085Na$_2$O:0.0013B$_2$O$_3$:0.01R:SiO$_2$:6.88H$_2$O

The mixture was transferred to an autoclave and heated to 240° C. with a ramp rate of 25° C./hr. The crystallization was continued for 24 hrs at 240° C.

After crystallization a solid product was recovered from the crystallization mixture, washed, and dried at 120° C. XRD (FIG. 1) of the dried solid product showed it to be ZSM-50. The SEM image (FIG. 2) of the solid product showed cubic morphology. The yields, solids content, and hourly throughput are summarized in Table 1 below.

Comparative Example D

A synthesis mixture was prepared containing the following ingredients: a sodium aluminate solution (12.34 wt. % NaOH and 3.06 wt. % Al(OH)$_3$ in water, Alcoa Corporation, Pittsburgh, Pa., USA), a 50 wt. % solution of tetraethyl ammonium bromide (R) in water (Sachem Chemicals), Ultrasil VN 35P (92.4 wt. % of SiO$_2$) and a 50 wt. % NaOH solution in water. The synthesis mixture had the following molar composition:

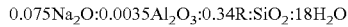
0.075Na$_2$O:0.0035Al$_2$O$_3$:0.34R:SiO$_2$:18H$_2$O

The mixture was transferred to an autoclave and heated to 138° C. with a ramp rate of 25° C./hr. The crystallization was continued for 72 hrs at 138° C.

After crystallization a solid product was recovered from the crystallization mixture, washed, and dried at 120° C. XRD of the dried solid product showed it to be ZSM-5. The yields, solids content, and hourly throughput are summarized in Table 1 below.

Example 3

A synthesis mixture was prepared containing the following ingredients: a sodium aluminate solution (12.34 wt. % NaOH and 3.06 wt. % Al(OH)$_3$ in water, Alcoa Corporation, Pittsburgh, Pa., USA), a 50 wt. % solution of tetraethyl ammonium bromide (R) in water (Sachem Chemicals), Ultrasil VN 35P (92.4 wt. % of SiO$_2$) and a 50 wt. % NaOH solution in water. The synthesis mixture had the following molar composition:

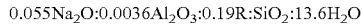
0.055Na$_2$O:0.0036Al$_2$O$_3$:0.19R:SiO$_2$:13.6H$_2$O

The mixture was transferred to an autoclave and heated to 240° C. with a ramp rate of 25° C./hr. The crystallization was continued for 24 hrs at 240° C.

After crystallization a solid product was recovered from the crystallization mixture, washed, and dried at 120° C. XRD of the dried solid product showed it to be ZSM-5. The yields, solids content, and hourly throughput are summarized in Table 1 below.

Comparative Example E

A synthesis mixture was prepared from water, Hexamethyleneimine (HMI) solution, Ultrasil Modified, sodium aluminate solution, and 50 wt. % sodium hydroxide solution The synthesis mixture had the following molar composition:

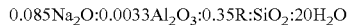
0.085Na$_2$O:0.0033Al$_2$O$_3$:0.35R:SiO$_2$:20H$_2$O

The mixture was crystallized at 150° C. in an autoclave with stirring at 250 RPM for 72 hours. After crystallization, the synthesis mixture slurry was filtered, washed with deionized (DI) water and dried at 120° C. The XRD patterns of the as-synthesized material showed the typical pure phase of MCM-22 topology. The resulting MCM-22 crystals had a SiO$_2$/Al$_2$O$_3$ molar ratio of ~23/1. The yields, solids content, and hourly throughput are summarized in Table 1 below.

Example 4

A synthesis mixture was prepared from water, Hexamethyleneimine (HMI) solution, Ultrasil, sodium aluminate solution, and 50 wt. % sodium hydroxide solution. The mixture had the following molar composition:

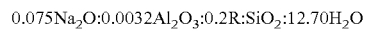
0.075Na$_2$O:0.0032Al$_2$O$_3$:0.2R:SiO$_2$:12.70H$_2$O

The mixture was crystallized at 205° C. in an autoclave with stirring at 250 RPM for 20 hours. After crystallization, the synthesis mixture slurry was filtered, washed with deionized (DI) water and dried at 120° C. The XRD patterns of the as-synthesized material showed MCM-22 topology with ZSM-5 impurity. ZSM-5 impurity was estimated to be <10% in the resulting product. The resulting MCM-22 crystals had a SiO$_2$/Al$_2$O$_3$ molar ratio of ~24. The yields, solids content, and hourly throughput are summarized in Table 1 below.

TABLE 1

| Example | Solid-content (wt. %) | Time (hrs) | Weight hourly throughput based on SiO$_2$ (hr$^{-1}$)* | Temperature (° C.) | Weight hourly template efficiency (hr$^{-1}$)* |
|---|---|---|---|---|---|
| A | 5.7% | 165 | 0.00030 | 171 | 0.014 |
| B | 13.3% | 72 | 0.00157 | 138 | 0.013 |
| 1 | 16.7% | 8 | 0.01771 | 250 | 0.038 |
| C | 15.9% | 72 | 0.00187 | 160 | 0.03 |
| 2 | 48.4% | 24 | 0.01716 | 240 | 0.089 |
| D | 18.5% | 72 | 0.00219 | 138 | 0.01 |
| 3 | 24.5% | 24 | 0.00868 | 240 | 0.054 |
| E | 16.7% | 72 | 0.00197 | 150 | 0.022 |
| 4 | 26.2% | 20 | 0.01115 | 205 | 0.136 |

*Estimate at 85% SiO$_2$ utilization

All patents, patent applications, test procedures, priority documents, articles, publications, manuals, and other documents cited herein are fully incorporated by reference to the extent such disclosure is not inconsistent with the present invention and for all jurisdictions in which such incorporation is permitted.

When numerical lower limits and numerical upper limits are listed herein, ranges from any lower limit to any upper limit are contemplated.

While the illustrative embodiments of this invention have been described with particularity, it will be understood that various other modifications will be apparent to and can be readily made by those skilled in the art without departing from the spirit and scope of this invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

We claim:
1. A process for converting hydrocarbons comprising the step of contacting said hydrocarbons under conversion conditions with a crystalline molecular sieve having a pore size in the range of from about 2 to about 19 Å, said molecular sieve made by a method comprising the steps of:

(a) providing a mixture comprising at least one source of ions of tetravalent element (Y), at least one trivalent element hydroxide source (OH⁻), and water, said mixture having a solid-content in the range of from about 20% to about 30%, wherein said solid-content is measured as the weight of said tetravalent element and said weight of said trivalent element expressed in terms of their oxides divided by the weight of said water in said mixture as a percentage:

$$\text{solid-content} = \frac{\text{said weight of said oxides in said mixture} \times 100\%}{\text{said weight of said water in said mixture}}$$

and (b) treating said mixture to form said crystalline molecular sieve with stirring at crystallization conditions sufficient to obtain a weight hourly throughput from about 0.005 to about 1 hr⁻¹, wherein said crystallization conditions comprise a temperature in the range of from about 200° C. to about 500° C. and a crystallization time less than 100 hr, wherein said crystalline molecular sieve has a zeolite framework type of MFI.

2. The process recited in claim 1, wherein said crystalline molecular sieve formed in step (b) is substantially free of non-crystalline material.

3. The process recited in claim 1, wherein said weight hourly throughput is in the range of from about 0.008 to about 1 hr⁻¹.

4. The process recited in claim 1, wherein said mixture comprises a structure-directing agent.

5. The process recited in claim 1, wherein said temperature range is from about 225° C. to about 250° C.

6. The process recited in claim 1, wherein said mixture further comprises from about 0.01 to 20 wt. % based on the total weight of said mixture of at least one seed source.

7. The process recited in claim 1, wherein said trivalent element is aluminum.

8. The process recited in claim 1, wherein said crystallization temperature is in the range of from about 200° C. to about 300° C., and crystallization time is less than 72 hr.

9. The process recited in claim 1, wherein said crystallization temperature is in the range of from about 200° C. to about 250° C., and crystallization time is less than 5 hr.

10. The process recited in claim 1, wherein said crystalline molecular sieve comprises ZSM-5.

11. The process recited in claim 1, wherein said tetravalent element is silicon.

12. The process recited in claim 1, further comprising the step of: (c) separating said MFI framework type crystalline molecular sieve.

* * * * *